US012046353B2

United States Patent
Garriga Calleja et al.

(10) Patent No.: US 12,046,353 B2
(45) Date of Patent: *Jul. 23, 2024

(54) ADMINISTERING EXPOSURE TREATMENTS OF A COGNITIVE BEHAVIORAL THERAPY USING A SMARTPHONE APP

(71) Applicant: Koa Health Digital Solutions S.L.U., Barcelona (ES)

(72) Inventors: Roger Garriga Calleja, Barcelona (ES); Iñaki Estella Aguerri, Barcelona (ES)

(73) Assignee: KOA HEALTH DIGITAL SOLUTIONS S.L.U., Barcelona (ES)

( * ) Notice: Subject to any disclaimer, the term of this patent is extended or adjusted under 35 U.S.C. 154(b) by 0 days.

This patent is subject to a terminal disclaimer.

(21) Appl. No.: 18/227,680

(22) Filed: Jul. 28, 2023

(65) Prior Publication Data

US 2023/0377716 A1 Nov. 23, 2023

Related U.S. Application Data

(63) Continuation of application No. 17/365,283, filed on Jul. 1, 2021, now Pat. No. 11,756,671.

(51) Int. Cl.
*G16H 20/70* (2018.01)
*A61B 5/00* (2006.01)
(Continued)

(52) U.S. Cl.
CPC .............. *G16H 20/70* (2018.01); *A61B 5/11* (2013.01); *A61B 5/165* (2013.01); *A61B 5/6898* (2013.01);
(Continued)

(58) Field of Classification Search
CPC ......................... G16H 50/20; A61B 2560/0242
(Continued)

(56) References Cited

U.S. PATENT DOCUMENTS

2016/0140864 A1  5/2016  Forman et al. ......... C09B 19/00
2017/0319123 A1  11/2017  Voss et al. ............... A61B 5/16
(Continued)

FOREIGN PATENT DOCUMENTS

WO   WO 2020/059789   9/2019
WO   WO 2020/0059789  9/2019
(Continued)

OTHER PUBLICATIONS

J. Callan et al., "Use of Computer and Mobile Technologies in the Treatment of Depression," Archives of Psychiatric Nursing, W.B. Saunders, Amsterdam, NL, vol. 31, No. 3, Nov. 4, 2016, pp. 311-318 XP085003278.

(Continued)

*Primary Examiner* — Fabricio R Murillo Garcia
(74) *Attorney, Agent, or Firm* — MARSHALL, GERSTEIN & BORUN LLP

(57) ABSTRACT

A method for administering an exposure treatment of a cognitive behavioral therapy (CBT) uses a mobile app and a server application. A user state of a patient undergoing a first step of the CBT based on the patient's condition during the first step is detected by sensors of the patient's smartphone. A situational state of the patient's surroundings during the first step is detected by the smartphone sensors. The mobile app determines whether the patient has made progress performing the first step. A user prompt is generated based on the user state and situational state. A next step of the CBT is configured based on the user state and situational state. The characteristics of the user prompt are generated using machine learning based on past task completions by the patient and other users so as to increase the likelihood that the patient will complete the next step of the CBT.

20 Claims, 6 Drawing Sheets

INSTRUCT USER TO PERFORM AN ACT
OF THE OVERALL EXERCISE TASK

(51) Int. Cl.
 *A61B 5/11* (2006.01)
 *A61B 5/16* (2006.01)
(52) U.S. Cl.
 CPC .... *A61B 5/7264* (2013.01); *A61B 2560/0493* (2013.01); *A61B 2562/0219* (2013.01)
(58) Field of Classification Search
 USPC .................................................. 340/539.12
 See application file for complete search history.

(56) References Cited

U.S. PATENT DOCUMENTS

| | | | |
|---|---|---|---|
| 2019/0246968 A1 | 8/2019 | Matic et al. | A61B 5/16 |
| 2021/0391083 A1* | 12/2021 | Moturu | G09B 19/00 |
| 2021/0401337 A1* | 12/2021 | Flickinger | A63F 13/215 |
| 2022/0300787 A1* | 9/2022 | Wall | G06N 20/00 |

FOREIGN PATENT DOCUMENTS

| | | |
|---|---|---|
| WO | WO 2020/223600 | 5/2020 |
| WO | WO 2020/0223600 | 5/2020 |
| WO | WO 2020/254127 | 6/2020 |
| WO | WO 2020/0254127 | 6/2020 |

OTHER PUBLICATIONS

Office action dated Sep. 18, 2023 from the European Patent Office in the related foreign application EP21199455.3 (14 pages).
Extended European Search Report dated Mar. 11, 2022, from the European Patent Office in the related foreign application EP21199455.3 (8 pages).

* cited by examiner

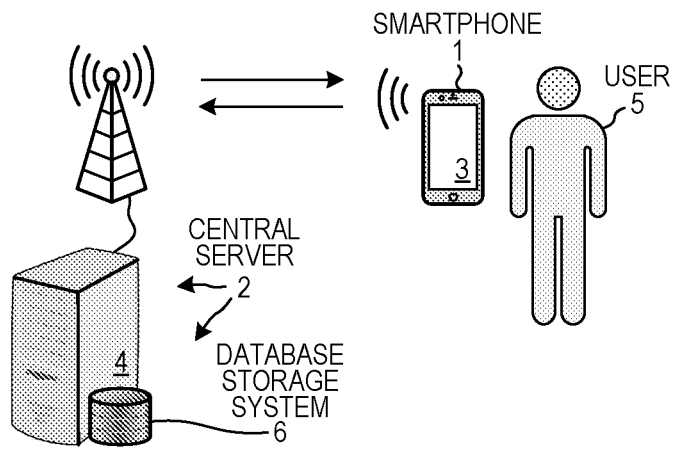

FIG. 1

USER PROFILE:
  GENDER: MALE
  AGE: 23
  MARITAL STATUS: MARRIED
  EMPLOYMENT: PART TIME
  DIAGNOSED DISORDER: OBSESSIVE COMPULSIVE DISORDER
  SUBTYPE DIAGNOSED DISORDER: CONTAMINATION / MENTAL CONTAMINATION
  QUESTIONNAIRE RESUTLS:
    YBOCS SCORES:
      OBSESSION SUBSCALE: 12
      COMPULSION SUBSCALE: 9
      TOTAL: 21
  OCI SCORES:
    WASHING SUBSCALE: 21
    CHECKING SUBSCALE: 12
    DOUBTING SUBSCALE: 5
    ORDERING SUBSCALE: 14
    OBSESSIVE SUBSCALE: 11
    HOARDING SUBSCALE: 3
    MENTAL NEUTRALIZING SUBSCALE: 8
    TOTAL: 74

USER PROFILE

FIG. 4

OPERATION OF APP ON SMARTPHONE

USER STATE:
  CURRENT STRESS LEVEL (FUNCTION OF ACCELEROMETER, NOISE, OTHER EXTERNAL SENSORS SUCH AS ELECTRODERMAL ACTIVITIY)
  DETECTED USAGE OF RITUALS (FUNCTION OF VIDEO AND AUDIO INPUT)
  DETECTED SEEKING FOR REASSURANCE (FUNCTION OF VIDEO AND AUDIO INPUT)
  CURRENT USER STRUGGLE (FUNCTION OF CURRENT STRESS LEVEL, PAST STRESS LEVEL, CURRENT AND PAST USAGE OF RITUALS AND REASSURANCE, CURRENT AND PAST TASK COMPLETION STATE)

SITUATIONAL STATE:
  PROXIMITY OF USER VERSUS THE OBJECT OF INTEREST (FUNCTION OF VIDEO INPUT)
  PROXIMITY OF USER VERSUS OTHER OBJECTS WITHIN THE SPACE (FUNCTION OF VIDEO INPUT)
  SCENE MAPPING (FUNCTION OF VIDEO INPUT)
  LIGHT INTENSITY (FUNCTION OF VIDEO INPUT AND SMARTPHONE LIGHT SENSOR)
  BACKGROUND NOISE (FUNCTION OF AUDIO INPUT)
  NUMBER OF PEOPLE IN THE SITUATION (FUNCTION OF VIDEO INPUT)

TASK COMPLETION STATE:
  NUMBER OF TIMES ACTION IS TAKEN
  PROXIMITY TO TARGET
  TIME PERFORMING THE ACTION OF INTEREST
  PERCENTAGE OF TASK COMPLETION

EXPERIENCE DATA:
  TASK NAME
  TRIAL NUMBER
  LEVEL OF INTENSITY
  INITIAL SCTD
  TIME IN TASK
  TASK COMPLETED
  LIST OF USER STATES WITH TIMESTAMPS
  LIST OF SITUATIONAL STATES WITH TIMESTAMPS
  LIST OF COMPLETION STATES WITH TIMESTAMPS
  LIST OF DECISIONS TAKEN WITH TIMESTAMPS:
    CONTINUE/UPDATE/STOP/COMPLETE
    MESSAGE PARAMETERS:
      COMMUNICATION CHANNEL
      TONE (MOTIVATING, NEUTRAL, IMPERATIVE, SERIOUS, RELAXING)
      CADENCE
      MESSAGE CONTENT

TASK EXPERIENCE
DATA FOR A TASK

FIG. 5

INSTRUCT USER TO PERFORM AN ACT
OF THE OVERALL EXERCISE TASK

ADMINISTERING EXPOSURE TREATMENTS OF A COGNITIVE BEHAVIORAL THERAPY USING A SMARTPHONE APP

CROSS REFERENCE TO RELATED APPLICATION

This application is a continuation of, and claims priority under 35 U.S.C. § 120 from, nonprovisional U.S. patent application Ser. No. 17/365,283 entitled "Administering Exposure Treatments of a Cognitive Behavioral Therapy Using a Smartphone App," filed on Jul. 16, 2021, the subject matter of which is incorporated herein by reference.

TECHNICAL FIELD

The present invention relates to cognitive behavioral therapies for overcoming obsessive compulsive disorders through the guided exposure to anxiety triggers administered using a smartphone app.

BACKGROUND INFORMATION

Cognitive behavioral therapy (CBT) is a form of psychotherapy based on both cognitive and behavioral principles designed to modify a patient's irrational thinking and behavior. CBT is used to treat behavioral conditions that cannot be controlled through rational thought, but rather result from earlier environmental conditioning. Such treatable conditions include adult anxiety disorders such as obsessive compulsive disorder (OCD).

The basis for CBT treatments is the controlled exposure of the patient to the situation or object that causes the anxiety. The therapist encourages the patient directly to confront the feared situation or object. By exposing the patient to the anxiety trigger, the prior environmental conditioning can be undone, and the patient's undesired subconscious adverse response to the situation or object can be unlearned. Conventionally, the exposure therapy of a CBT program is administered in face-to-face sessions between the therapist and the patient in which the patient performs an exposure assignment. If the exposure assignment is too difficult, the therapist must recognize the patient's inability to proceed with the treatment and suggest an easier assignment.

The success of the CBT program depends on the ability of the therapist to assess the patient's engagement in the exposure therapy and to encourage the patient to complete each successively more difficult assignment. However, the cost of a human therapist to accompany the patient in every step of the exposure treatment is prohibitively expensive in many cases. CBT programs can be more cost effectively administered through an interactive computer interface instead of requiring a human therapist to be physically present. However, even having a human therapist being remotely present for the exposure treatment is expensive.

A system is sought that can replace the human therapist in a CBT program, but yet that can monitor the patient's progress, provide encouragement to the patient, and suggest easier or more difficult exposure assignments at the appropriate times.

SUMMARY

A method for administering an exposure treatment of a cognitive behavioral therapy (CBT) is performed using a mobile app and a server application. The CBT involves the controlled exposure of a patient to an object that causes the patient to experience anxiety. A user state is detected of the patient while the patient is currently Undergoing a first step of the CBT. The user state is based on the patient's behavior and physiological condition during the first step of the CBT as detected by sensors of a smartphone used by the patient. A situational state is detected of the patient's surroundings while the patient is undergoing the first step of the CBT. The situational state is detected by sensors of the smartphone used by the patient. The mobile app controls the detection of the user state and the situational state. The mobile app determines whether the patient has performed the first step in a manner that achieves progress in the CBT. Whether the patient has achieved progress in the CBT is determined based on the stress level and the struggle level of the patient during the first step. The stress level of the patient during the first step is determined based on touch interaction data and motion data detected by sensors on the smartphone during the first step.

A verbal user prompt is generated based on the detected user state and the detected situational state during the first step. The verbal user prompt is output by a loudspeaker of the smartphone. A next step of the CBT is configured based on the detected user state and the detected situational state during the first step. The next step of the CBT is also configured using machine learning based on the past task completions by the patient and other users so as to minimize how many steps are required for the patient to complete the CBT.

The content and character of the verbal user prompt is generated using machine learning based on past task completions by the patient and other users in order to make it more likely that the patient will complete the next step of the CBT. The machine learning generates the content of the verbal user prompt so as to include a level of reassurance most likely to motivate the patient to proceed with the next step of the cognitive behavioral therapy. The character of the verbal user prompt is defined by parameters such as the tone of the voice, the pitch of the voice, and the cadence of the verbal user prompt. The machine learning that generates the verbal user prompt is performed by a deep neural network.

In another embodiment, a system for administering an exercise task of an exposure treatment includes a smartphone, a central server and a database storage system. Data regarding past therapy steps by the patient and other users is stored in the database storage system. Instructions of a mobile application are stored in the device memory of the smartphone. Instructions of a server application are stored in the server memory of the central server. The instructions of the mobile application when executed cause the smartphone to detect a user state and a situational state of a patient currently undergoing a first step of a CBT, determine whether the patient has achieved progress in performing the first step, and output a user prompt based on the user state and situational state detected during the first step. The user state is based on the patient's behavior and physiological condition during the first step as detected by sensors of the smartphone. The situational state of the patient's surroundings while the patient is undergoing the first step is also detected by the sensors of the smartphone.

The instructions of the server application when executed cause the central server to generate the user prompt using machine learning based on past therapy steps by the patient and other users of the mobile application so as to have a content and character adapted to influence the patient to complete the next step of the CBT. The instructions of the server application also configure the next step of the CBT based on the user state and situational state detected during the first step.

The mobile application determines whether the patient has achieved progress in the CBT based on the stress level of the patient during the first step. The stress level of the patient during the first step is determined based on touch interaction data and motion data detected by the sensors of the smartphone during the first step. The touch interaction data is sensed by a touchscreen of the smartphone, and the motion data is sensed by an accelerometer of the smartphone.

Further details and embodiments and methods and techniques are described in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

FIG. 1 is a simplified diagram of a system used to administer an exposure treatment of a cognitive behavioral therapy.

FIG. 4 shows the form of a user profile generated by the method for administering an exposure treatment.

FIG. 5 shows the form of task experience data collected by a mobile app performing the method for administering an exposure treatment.

DETAILED DESCRIPTION

Figure 2:
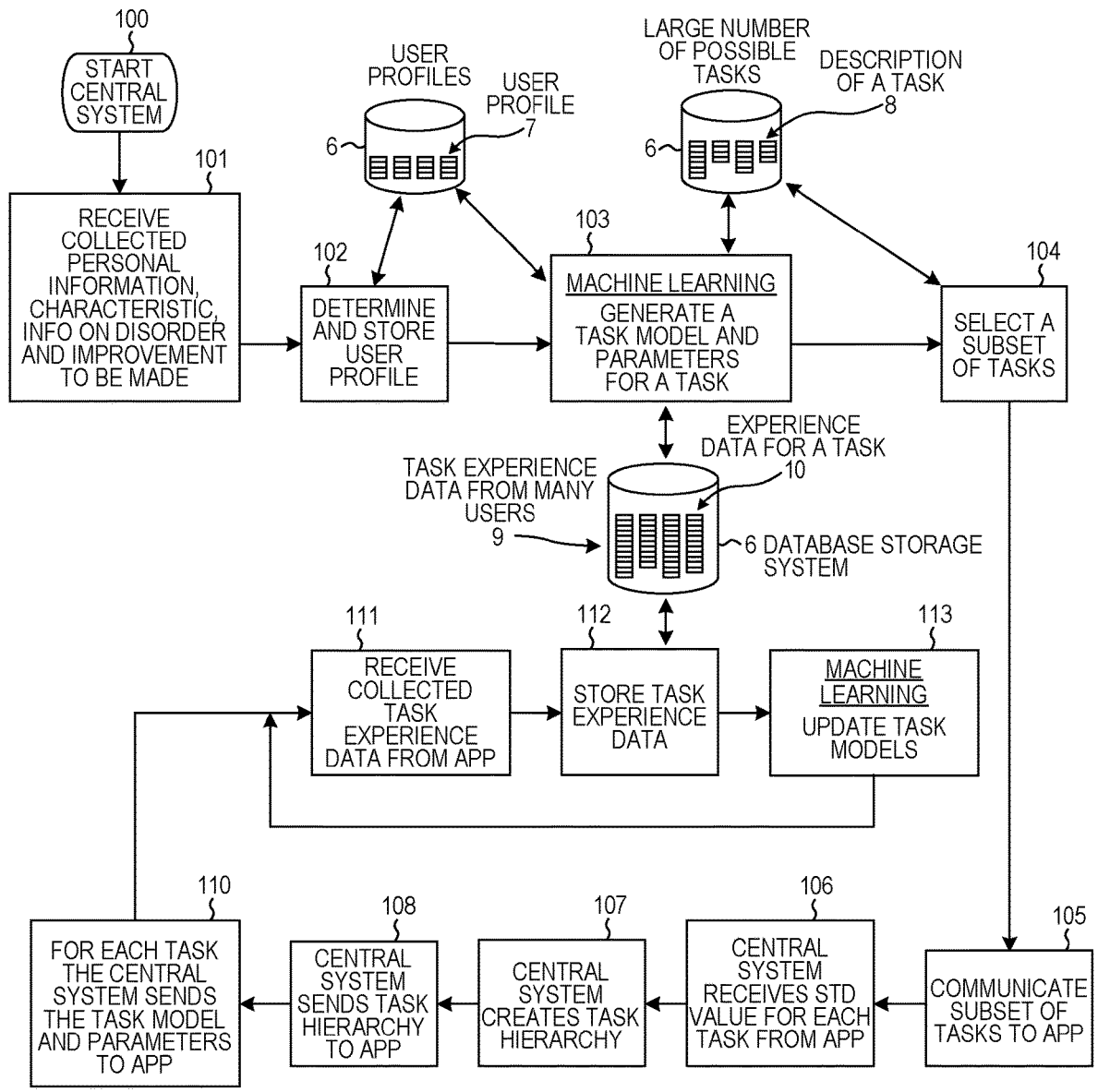
FIG. 2 is a flowchart illustrating the operation of server software in a novel method for administering an exposure treatment.

Reference will now be made in detail to some embodiments of the invention, examples of which are illustrated in the accompanying drawings.

FIG. 1 is a diagram of a system used to administer an exposure assignment of a cognitive behavioral therapy (CBT). A novel method for administering the exposure treatment is performed using the system. The system includes a smartphone 1 and a central server 2. The method is implemented using a mobile application ("app") 3 running on smartphone 1 and central server software 4 running on central server 2. Mobile app 3 is stored in a device memory of smartphone 1, and central server software 4 is stored in server memory of central server 2. Central server software 4 includes a server application that works together with mobile app 3. The user 5 of app 3 is a patient undergoing the exposure treatment. As the patient 5 is undergoing the exposure treatment, app 3 on smartphone 1 sends collected task experience data to central server 2, where the data is stored in a database storage system 6.

Figure 3:
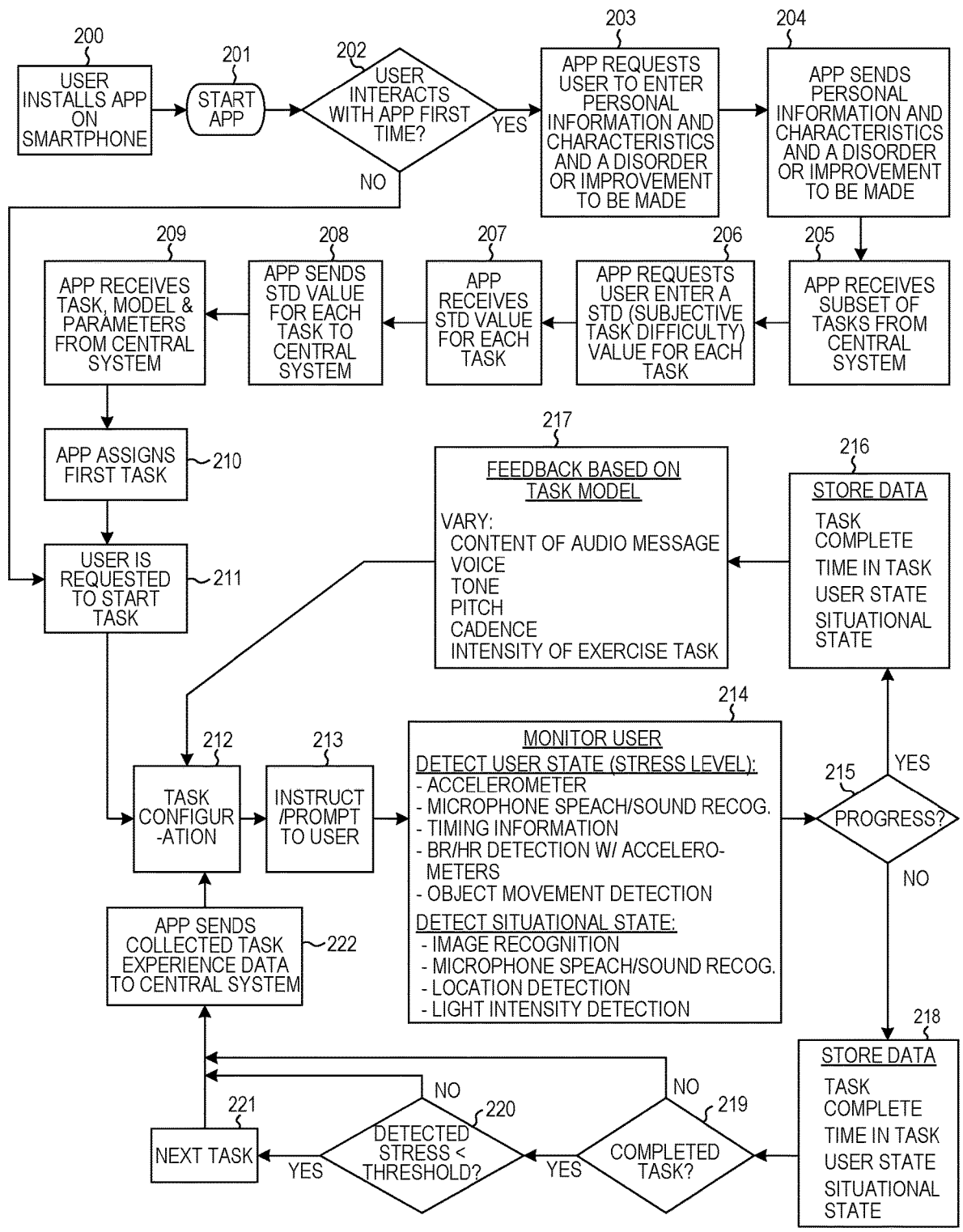
FIG. 3 is a flowchart illustrating the operation of a mobile app in the novel method for administering an exposure treatment.

FIG. 2 is a simplified diagram illustrating the operation of server software 4. FIG. 3 is a simplified diagram illustrating the operation of mobile app 3, which is the application program that together with the server application of server software 4 administers the cognitive behavioral therapy. App 3 and server software 4 execute simultaneously. Steps 100-113 of FIG. 2 are steps of central server software 4, whereas steps 200-222 of FIG. 3 are steps of app 3.

The cognitive behavioral therapy cannot begin until patient 5 installs app 3 on his or her smartphone 1. FIG. 3 begins with step 200, in which user 5 installs app 3 on smartphone 1, and app 3 starts running in step 201. If it is determined in step 202 that user 5 is using app 3 for the first time, then app 3 requests and prompts user 5 in step 203 to enter personal information and characteristics and a disorder or improvement to be made. Examples of personal information and characteristics include age, sex, weight, height, medical issues and conditions, the user's profession, amount of daily physical exercise, and eating habits. Examples of disorders include obsessive-compulsive disorder (OCD), phobias, panic disorders, social anxiety disorder, post-traumatic stress disorder, and generalized anxiety disorder. An example of an improvement to be made is a muscle or body part to be strengthened or conditioned. One embodiment described herein involves OCD and a phobia for touching dirty objects. The improvement sought is the ability to touch an object that is perceived to be dirty without washing ones hands immediately. This phobia can be overcome with an exposure treatment.

In step 203, app 3 queries user 5 for this personal information using a series of visual prompts provided to user 5 on the touchscreen of smartphone 1. User 5 responds by making appropriate selections on the touchscreen of the smartphone and entering information text. In step 204, app 3 sends the collected information to the central server 2 via wireless cellular telephone communication. As seen in the flowchart of FIG. 2, the server application of server software 4 (step 100) and then receives (step 101) the personal information and characteristics and information on the disorder and improvement to be made. In step 102, central server software 4 then stores the collected information in database storage system 6 and assembles the information in the form of a user profile 7.

FIG. 4 shows the form of an exemplary user profile 7. There is one such user profile stored in database storage system 6 for each of a plurality of users of the system. A user is sometimes referred to herein as a "patient". Database storage system 6 also stores a large number of descriptions of possible exercise tasks. Reference numeral 8 in FIG. 2 identifies one such description of an exercise task. Examples of exercise tasks include exposure treatment tasks, touching a bathroom door handle exercise task, touching a toilet flush handle exercise task, touching a toilet seat exercise task, putting a hand in toilet bowl water exercise task, touching a toilet wall exercise task, touching the bottom of a shoe exercise task, touching raw poultry or hamburger meat exercise task, shaking hands with a stranger exercise task, pressing a button on a vending machine exercise task, handling money exercise task, leaving one's locked house without rechecking the door exercise task, turning off the stove and leaving the room without rechecking exercise task, refraining from phoning one's partner to check that they arrived at work exercise task, and physical exercise tasks such as lifting a barbell exercise task, stretching a stretchable cord exercise task, squeezing a squeezable ball exercise task, taking a walk outdoors exercise task, eating by a certain hour of the day exercise task, a breathing exercise task, a sit-ups exercise task, and a conversation with a friend exercise task. There is one task description for each of the possible tasks.

The remaining steps of the novel method of FIGS. 2-3 are explained with reference to an exemplary exposure treatment to overcome the phobia of touching a toilet flush handle. In step 103, a machine learning process 103 in central server software 4 maintains and uses the descriptions of tasks as they are stored in database storage system 6. A subset of the tasks is selected in step 104 based on user profile 7 of user 5, task experience data 9 collected previously for the various tasks, and the descriptions of tasks as they are stored in database storage system 6. In step 105 of FIG. 2, the subset of the tasks is communicated to app 3 on smartphone 1. In step 205 of FIG. 3, app 3 receives the subset of tasks from central server system 2 and prompts user 5 to enter Subjective Task Difficulty (STD) information pertaining to each of the tasks of the subset of tasks. This may involve prompting user 5 via the touchscreen of smartphone 1 to rank the exercise tasks in order according to the user's belief as to how much stress or effort (struggle) would be involved were user 5 to performs the tasks. In step 207, app 3 receives this STD information for each task of the subset of tasks. In step 208, app 3 communicates this collected STD information to central server system 2. In step 106 of FIG. 2, the STD information is received by central server system 2. In step 107, central server system 2 creates a hierarchy of the tasks in an order that user 5 can then attempt to perform. In step 108, central server system 2 communicates this task hierarchy back to app 3. In step 110, central server system 2 sends a task model and parameters to app 3 for each task in the hierarchy.

In step 209 of FIG. 3, app 3 receives the task models and parameters. Then app 3 assigns a first task for user 5 to perform in step 210, and requests user 5 to start the first task in step 211. App 3 does this, for example, by playing an audio message that is output from the loudspeaker of smartphone 1. After the task model and the particular circumstances of the exercise are configured (step 212), app 3 prompts user 5 to perform a first act of the exercise task in step 213. In the case of touching the flush handle of a toilet exercise task, the instruction or prompt may be an audio or verbal instruction to place the smartphone in the user's right hand. The type of voice used (female voice, male voice), the tone of the voice, the pitch of the voice, and the cadence of the message are determined by the parameters that were configured in step 212. In step 214, app 3 then uses the sensors and detectors of smartphone 1 to monitor user 5 as the user attempts to perform the first act of the assigned task. Physical quantities and occurrences are detected and sensed by smartphone 1 to make a determination as to a "user state". Physical quantities and occurrences are also detected and sensed to make a determination as to a "situational state". For example, the detected data is sensed by an accelerometer, a camera, a microphone, or a touchscreen of smartphone 1.

Examples of physical quantities and occurrences detected in order to determine "user state" include: the hand of user 5 shaking as detected by the accelerometer of smartphone 1, the detected amount of time user 5 spends performing a prompted act, an audio response uttered by user 5 as detected by the smartphone microphone and detected by voice recognition performed by smartphone 1. User 5 may, for example, be detected to have stated, "okay, I have done it," or "I can't do this."

Examples of physical quantities and occurrences are detected and sensed to make a determination as to the "situational state" include detected proximity to objects, scene mapping, detected intensity of light, GPS coordinates, relative detected movement from a previously determined position of the smartphone, detection of other individuals speaking or making noises, and detection of background noises and sounds.

In decision step 215, if app 3 determines that user 5 has made progress in performing the assigned act of an exercise task, then collected data is stored in step 216. This information is temporarily stored on smartphone 1. In step 217, app 3 uses the task model to generate feedback to provide to user 5 and/or to determine how to proceed in prompting user 5 to continue performing the assigned act of the exercise task. If, for example, user 5 is struggling to perform the assigned act that user 5 has been prompted to perform, and user 5 has not completed the act, the feedback may determine another audio message to be output to user 5 via the smartphone speaker. Such a message may, for example, be "you can do it." The feedback determines the content of the message as well as the voice, tone, pitch and cadence. In this way, the conversation between user 5 and smartphone app 3 can be modified and tailored for the particular user so that app 3 is more comforting, reassuring and soft. Alternatively, app 3 can be more firm, strong and confident in its communication with user 5. App 3 performs steps 212-217 of the method repeatedly as user 5 carries out the various discrete assigned acts of the exercise task. In the example of the exercise task "touching toilet flush handle", user 5 is prompted in step 213 by audio message to use the user's right hand to take a photograph of user 5 touching the toilet flush handle with the user's left hand. For example, app 3 causes a verbal user prompt in the form of an audio message "snap the picture—you can do it" to be output from the loudspeaker of smartphone 1. App 3 places smartphone 1 in the camera mode so that the pressing of the camera shutter icon by user 5 causes the image on the screen to be captured as digital image data.

Returning to decision step 215, if app 3 determines that user 5 has not made progress in carrying out the assigned act of the exercise task, then in step 218 app 3 stores the latest task completion information, user state information, and situational state information. This information is temporarily stored on smartphone 1. In step 219, if app 3 determines that the exercise task has not been completed, then in step 222, app 3 sends the collected task experience data to the central server system 2. One way that app 3 can determine that the task has not been completed is if the user is prompted in step 213 to take a photograph of the exercise completion act, and app 3 detects no such image having been taken. Then user 5 may be provided with an audio prompt to verbally indicate that user 5 did not complete the assigned act of the exercise task. Speech recognition functionality of smartphone 1 (either performed entirely locally on the smartphone, or performed partially on central server system 2) is used for this speech recognition purpose. In step 219, if app 3 determines that the exercise completion act has been completed, then app 3 determines in step 220 whether the detected user state has a particular desired characteristic. In the case of the assigned act being a physically intensive exercise, the detected user state might be the physical fatigue of user 5 and whether the exercise completion act took more than a predetermined amount of time to complete. In the case of the exercise task being "touching the toilet flush handle", the detected user state might be a detected stress level of user 5. In step 220, app 3 determines whether the detected user stress level in carrying out the task was below a predetermined threshold of user stress. If the determined user stress is still above the maximum desired level, then app 3 prompts user 5 to perform the same exercise task again until the user's detected stress level drops below the desired threshold. Once app 3 determines in step 220 that the user state has the particular desired characteristics, in step 221 app 3 sets the current assigned act to be the next exercise task in the task hierarchy. For example, the user state would have the desired characteristics in step 220 if user 5 performed the "touching the toilet flush handle" task, and the user's detected stress level in doing so was below the maximum desired stress level. Then app 3 would proceed in step 221 to the next task of the task hierarchy. In step 222, app 3 sends the collected task experience data 10 to central server system 2.

FIG. 5 shows the form of exemplary task experience data 10 collected by app 3. In this example, the collected task experience data 10 is for the "touching the toilet flush handle" exercise task. The task experience data 10 includes parameters for the user state, the situational state, the task completion state and experience data.

In step 112 of FIG. 2, this task experience data 10 is received by central server system 2. In step 112, data 10 is stored in database storage system 6. As more and more instances of task experience data 10 are collected over time, the machine learning process performed in step 113 updates the task models and parameters to optimize the various adjustable aspects of the interaction with user 5 in order to optimize the successful completion of the exercise task by the user. For example, using a deep neural network, the machine learning process generates the content of the verbal user prompts to include a level of reassurance most likely to motivate the user to proceed with the next step of the exercise task. Each set of task experience data includes an indication of the satisfactory/unsatisfactory nature of the exercise performance, along with a number of parameters that indicate what occurred and what was detected during the exercise.

Figure 6:
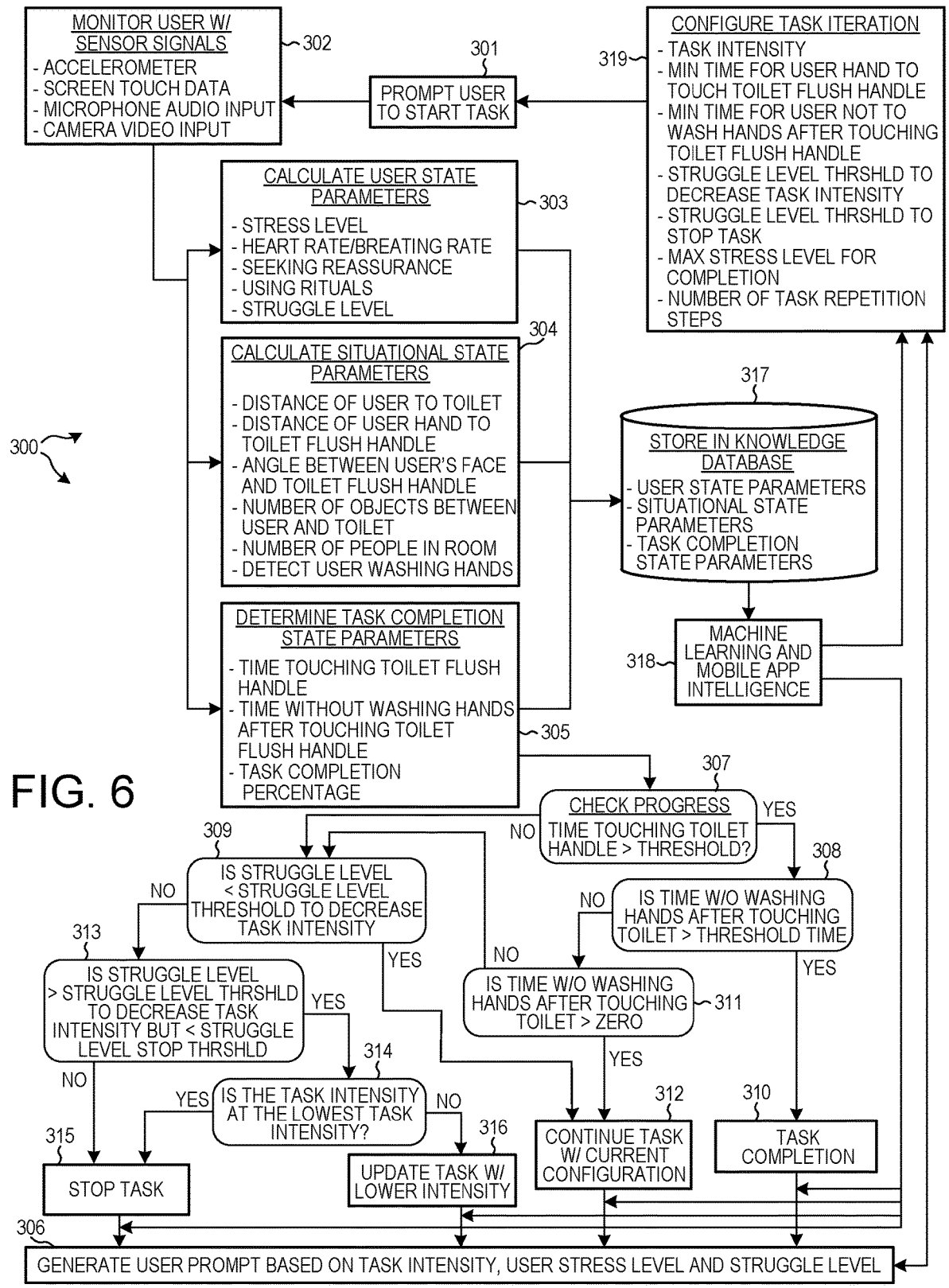
FIG. 6 is a flowchart of steps of the novel method for administering the exemplary exposure treatment of touching a toilet flush handle.
Figure 7:
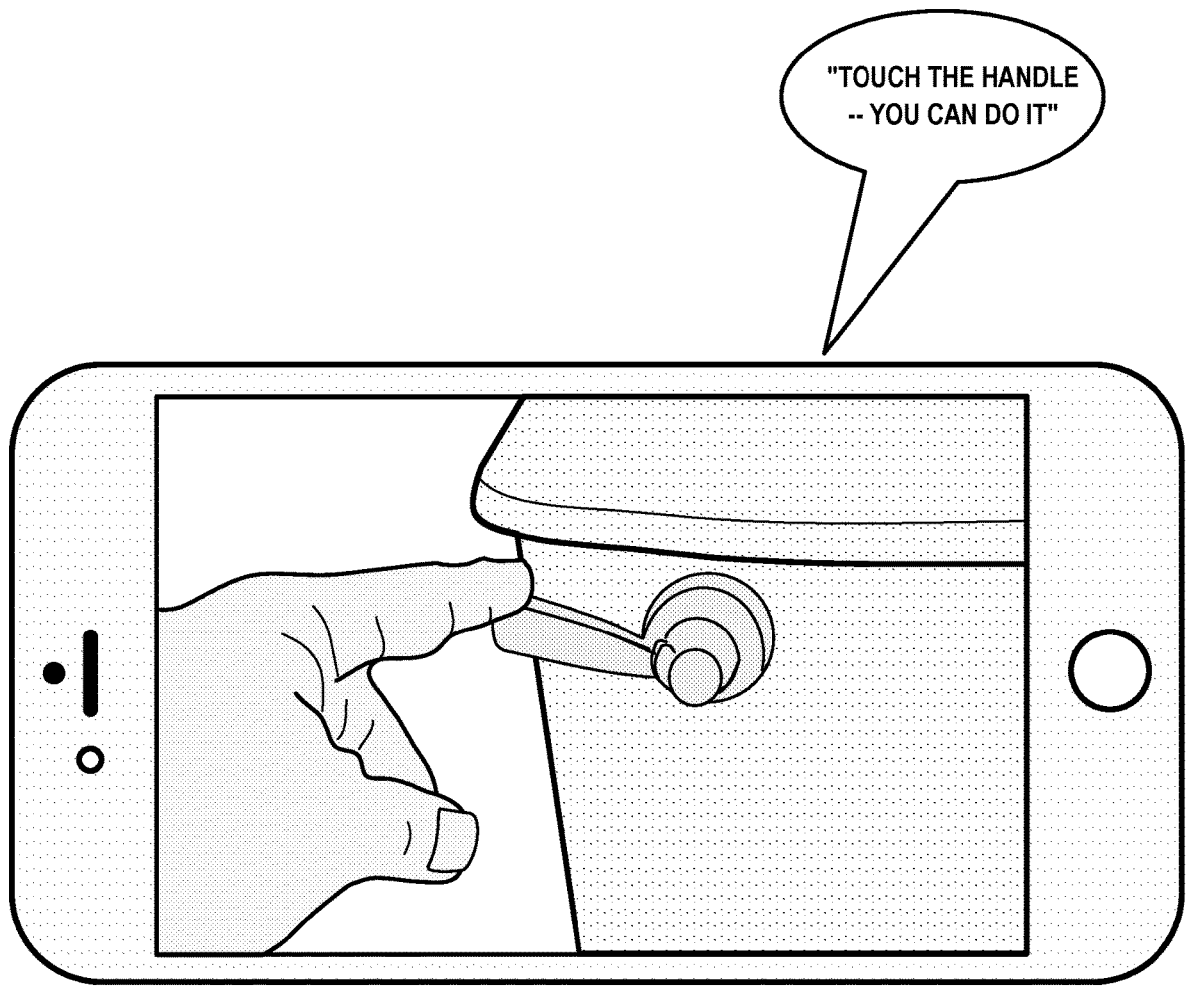
FIG. 7 illustrates a video image taken by the user's smartphone while the user is performing the exemplary exposure treatment of FIG. 6.

FIG. 6 is a flowchart of another embodiment of the novel method 300 for administering an exposure treatment that is directed to the exemplary exercise task of touching a toilet flush handle. Method 300 is performed using the system of FIG. 1 that includes smartphone 1 and central server 2. This embodiment of method 300 begins at step 301, in which app 3 prompts user 5 to perform a task that is part of the exposure treatment. In this example, app 3 generates an audio prompt requesting user 5 to touch the flush handle of a toilet with the left hand while making a video recording of the act using smartphone 1 in the right hand. FIG. 7 illustrates the video image that user 5 is recording with smartphone 1 while touching the flush handle with the user's finger. In this example, the verbal prompt is, "touch the handle—you can do it!" The tone, pitch, cadence and content of the verbal prompt is selected based on the personal information and phobia description entered by user 5 as matched by machine learning to the experience of other users with similar characteristics. In step 302, app 3 monitors user 5 using the sensors and detectors of smartphone 1 as user 5 attempts to perform the first step of the assigned task. Sensor signals are received from an accelerometer, a touchscreen, a microphone and a video camera. The motions of user 5 are detected indirectly through the movements of smartphone 1 as measured by an accelerometer in the phone. In addition, the touch interactions of user 5 with smartphone 1 are detected by a contact intensity sensor of the touchscreen, such as a piezoelectric force sensor, a capacitive force sensor, an electric force sensor or an optical force sensor. Touch interaction data includes contact with the touchscreen (a fingerdown event), the pressure of the contact, the size of the contact, movement of the contact across the touchscreen, and the end of the contact (a finger-up event).

In step 303, the data from the sensor signals is used to calculate "user state" parameters of user 5 during the task, such as stress level, struggle level, heart rate, breathing rate, and whether user 5 is seeking reassurance or is following rituals. Heart rate and breathing rate can be determined using accelerometer motion data. The user's breathing movement and beating heart are sensed by the accelerometer. App 3 uses the touch interaction data and the motion data to determine the current stress level of user 5. The user's struggle level with the current task is determined based on the motion data, the heart rate, the breathing rate and the audio input from the microphone, as well as the amount of time user 5 has spent performing the assigned task. For example, the audio input could be the voice recognition of the user's statement, "I can't do this."

In step 304, the data from the sensor signals is used to calculate "situational state" parameters of user 5 during the task. For the exemplary exercise task of touching a toilet flush handle, these "situational state" parameters include: distance of user 5 to toilet, distance of user's hand to toilet flush handle, angle between user's face and toilet flush handle, number of objects between user 5 and toilet, number of people in room, light intensity in the room, and whether user 5 washed his or her hands. For example, the audio input is used to determine the number of people in the room by detecting other individuals speaking or making noises. The video camera input is used to determine the distance of the user's hand to the toilet flush handle.

In step 305, app 3 determines the task completion state parameters based on the other parameters and on the data from the sensor signals. Examples of task completion state parameters are the time the user's hand was touching the toilet flush handle, the time elapsed after touching the handle before user 5 washed his or her hands, and the percentage of task steps completed.

In step 306, app 3 generates a real-time verbal user prompt based on the user's current stress level and struggle level, on the intensity of the current step of the exposure treatment task, and on the user's progress achieved in the current step. The flowchart of FIG. 6 shows the decision steps 307-316 that app 3 performs to generate the most appropriate verbal prompt based on the user state, the situational state during the current step of the task, and the task completion state. The most appropriate verbal prompt is the prompt that conveys a level of reassurance most likely to motivate the user to proceed with the next step of the exercise task.

In decision step 307, app 3 determines the progress user 5 has achieved in performing the current step of the exposure treatment task. In this example, app 3 determines whether the time user 5 spent touching the toilet flush handle exceeded a minimum time threshold, for example, one second in the first task step. App 3 determines the user's progress in performing the task based on the video camera input and the other sensor signals. If user 5 achieved the minimum time threshold, the decision flow proceeds to decision step 308; otherwise the decision flow proceeds to decision step 309.

In decision step 308, app 3 determines whether user 5 abstained from washing his or her hands after touching the toilet handle for a minimum time threshold, for example, thirty second in the first task step. If user 5 achieved the minimum time threshold, the decision flow proceeds to step 310; otherwise the decision flow proceeds to decision step 311. If user 5 refrained from washing his hands for the minimum time threshold associated with the first task step, then the first task step is completed in step 310, and a prompt is generated in step 306. After user 5 completes the first task step in step 310, the user is given an audio prompt such as, "Well done, you have completed the task. You are now ready to take on a more complicated version of the task."

Depending on the user stress level and struggle level and the intensity level of the first task step, app 3 generates a user prompt that instructs user 5 to proceed to a subsequent task step that has a greater intensity level. The intensity of the subsequent task step is selected to achieve the fastest completion of the exposure therapy attainable by user 5 based on both input from machine learning on the knowledge base 317 and mobile app intelligence analyzing the user and situational states.

When app 3 detects the user state parameters, the situational state parameters, and the task completion state parameters in steps 303-305, those parameters are transmitted to database storage system 6 and stored in knowledge base 317. In addition, knowledge base 317 includes parameters collected from cognitive behavioral therapies undertaken by other users. In step 318, machine learning is performed on knowledge base 317 in order to identify the characteristics of the subsequent task step that best match the capabilities of user 5 to complete the exposure therapy in the shortest time. In one embodiment, the machine learning is performed using a deep neural network. For example, the machine learning in step 318 might determine that user 5 is able to skip an intensity level so as to complete the overall exposure therapy in a shorter time. In step 319, machine learning and mobile app intelligence configure the characteristics of the subsequent task step. Examples of task configuration characteristics include task intensity, minimum time for the user's hand to touch the toilet flush handle, minimum time for the user not to wash hands after touching toilet handle, struggle level threshold to decrease intensity of next task step, struggle level threshold to stop task, maximum permitted stress level to consider task completed, and total number of task repetition steps.

The user prompt generated in step 306 after the task step is completed in step 310 includes both positive feedback regarding the current task step as well as encouragement and reassurance regarding the next task step, which is described to user 5 based on the task configuration performed in step 319.

Returning to the decision step 308, if user 5 is unable to refrain for the minimum time threshold from washing his or her hands, the decision flow proceeds to step 311, where app 3 determines whether user 5 immediately washed his or her hands after touching the toilet handle. If at least some time elapsed after touching the toilet handle and before washing hands, the decision flow proceeds to step 312; otherwise the decision flow proceeds to decision step 309. If user 5 waited some time between touching the handle and washing hands, then in step 312 the configuration of the next task step is maintained with the current configuration. A prompt is generated in step 306 encouraging user 5 to attempt the assigned task again with the current configuration. The tone of the prompt voice, the pitch of the prompt voice, and the cadence of the prompt message are determined using machine learning on the knowledge base 317 and mobile app intelligence analyzing the user state parameters and situational state parameters.

If in decision step 311, no time elapsed after touching the toilet handle and washing hands, the decision flow proceeds to step 309. The decision flow also proceeds to step 309 from step 307 if user 5 did not touch the toilet flush handle for at least the minimum time threshold. In decision step 309, app 3 determines whether the struggle level of user 5 during the first task step did not exceed the maximum struggle level threshold for decreasing the task intensity of the next task step. If the struggle level of user 5 during the first task step is less than (within) the maximum allowed struggle level threshold for decreasing the task intensity, then the decision flow proceeds to step 312, and the configuration of the next task step is maintained with the current configuration and intensity. If, however, the struggle level of user 5 during the first task step exceeds the maximum allowed struggle level threshold for decreasing the task intensity, then the decision flow proceeds to step 313.

In decision step 313, app 3 determines whether the struggle level of user 5 during the first task step both exceeds the maximum struggle level threshold for decreasing the task intensity and is less than the maximum struggle level threshold for stopping the exercise task. If the struggle level of user 5 during the first task step is between the struggle level threshold for decreasing the task intensity and the struggle level threshold for stopping the exercise, then the decision flow proceeds to step 314; otherwise the task is stopped in step 315.

In decision step 314, app 3 determines whether the task intensity level of the current task step is set at the lowest task intensity level. If the task intensity level of the current task step is already set at the lowest task intensity level, then the task is stopped in step 315. If, however, the task intensity level of the current task step is not set at the lowest task intensity level, the decision flow proceeds to step 316, in which the configuration of the next task step is modified to run with a lower task intensity level.

In addition, a prompt is generated in step 306 after both step 315 and step 316. If user 5 has stopped trying to complete the task in step 315, then the voice, tone, pitch, cadence and content of the audio prompt will be composed to motivate the user not to give up on the exposure therapy altogether. The audio prompt would be the most comforting, reassuring and soft. An example of the prompt content is, "Let's pause for now and continue another time. You showed improvement and are closer to completing the task." If user 5 will be prompted to repeat the task at a lower intensity level in step 316, an example of the prompt content would be, "Continue, focus on the task and don't look away. Feel the discomfort, but keep going for five more seconds." The tone of the prompt after step 316 would be somewhat firmer and confident than the tone of the prompt after step 315.

Machine Learning: As described above, the central server 2 receives many different task experience data sets from numerous smartphones used by many different users including smartphone 1, and performs machine learning using that data to optimize parameter values of a task model. In one example, the task model is a decision tree for a particular exercise. A parameter of that decision tree may, for example, have a threshold value. By machine learning, this threshold value is adjusted. After adjustment, the entire task model complete with all its parameter values (including the adjusted threshold value) is returned to the smartphone 1. The next time the user 5 uses smartphone 1, the new adjusted threshold value will be used in the decision tree to determine what next step in the decision tree to perform or proceed to. Each task experience data set includes task completion state information.

In order to determine the values of parameters of the decision tree (A), the machine learning method estimates the likelihood of successful task completion given the contextual information about the user and determines the parameter values as a function of the likelihood. This contextual information includes the user profile, the subjective task difficulty (STD) introduced by the user and information from previous "task experiences" (TE) the user had (e.g. number of times the user tried the exercise before, percentage of completion, minimum stress level in the tasks completed, stress level at the end of the last task trial, etc.). The contextual information is arranged as a numerical vector (S). The machine learning method (M) estimates the likelihood given S and a policy ($\mu$) as a function of the estimated likelihood can be used to make the decision. In one example, a contextual bandit method is used to determine the parameter values: Each time (t) that the central server 2 needs to select the parameter values for a user (u), the contextual information is computed as a function of the previous task experiences $S_{t,u} = f(TE_{1,u}, \ldots, TE_{t-1,u})$. Given $S_{t,u} \in R^n$, the central server 2 determines the decision parameter values for the decision tree $A_{t,u} \in R^m$, following a certain policy $\mu$ ($S_{t,u}$) (vector of probabilities of choosing each of the decision parameter values given $S_{t,u}$). Once the user finishes the task, the new $TE_{t,u}$ is received by the central server 2, which contains the result $R_{t,u}=1$ if the task was successfully completed or $R_{t,u}=0$ otherwise. The central server 2 uses the collected tuples $\{(S_{1,u}, A_{1,u}, R_{1,u}), \ldots, (S_{t-1,u}, A_{t-1,u}, R_{t-1,u})\}_u$ of all users u to determine the result $R_{t-1,u}$ as a function of the contextual information $S_{t-1,u}$ and the decision parameters $A_{t-1,u}$: $R_{t-1,u} = g_\theta (S_{t-1,u}, A_{t-1,u})$. This function $g_\theta$ is a machine learning model, e.g., a logistic regression or a feedforward neural network parameterized by the parameter vector $\theta$. The machine learning model is trained in all the collected tuples using the vector $S_{t-1,u}, A_{t-1,u}$ as features and $R_{t-1,u}$ as target for all users u, and time t to estimate the optimal parameter vector $\theta^*$. Then, when the parameter values of the decision tree need to be determined, the central server 2 uses the trained model ($g_{\theta^*}$) to estimate the result $R_{t,u}$ given $S_{t,u}$ for each possible value of the parameters of the decision tree. The central server 2 determines the updated model and parameter values according to a policy $\mu$. In one example, the policy $\mu$ is an $\epsilon$-greedy policy (epsilon-greedy reinforcement learning policy) that selects the decision tree parameter values with the highest estimated $R_{t,u}$ argmax$_{At,u}$ $g_{\theta^*}(S_{t,u}, A_{t,u})$ with probability (1–$\epsilon$) and any other decision tree parameter value randomly with probability $\epsilon$. Once determined, the updated model including its parameter values is sent to the smartphone 1.

Examples of methods usable to determine user state include: 1) An accelerometer-based method such as the stress detection method described in U.S. patent application Ser. No. 17/227,308, by Joao Guerreiro, entitled "Determining A Stress Level Of A Smartphone User Based On The User's Touch Interactions And Motion Sensor Data", filed Apr. 10, 2021 and published as US 2022/0322985 (the entire subject matter of which is incorporated herein by reference); and 2) A camera-based method such as is described in "Instant Stress: Detection of Perceived Mental Stress Through Smartphone Photoplethysmography And Thermal Imaging", by Youngjun Cho et al., JMIR Mental Health, Vol. 6, No. 4 (2019), or as explained in "VitaMon: Measuring Heart Rate Variability Using Smartphone Front Camera", by Sinh Huynh, et al., SenSys 2019: Proceedings of the 17th Conference On Embedded Networked Sensor Systems, New York, Nov. 10-13, 2019, pages 1-14. Examples of methods usable to determine situational state include: 1) "Learning To Detect Human-Object Interactions", by Yu-Wei Chao, et al., IEEE Winter Conference on Applications Of Computer Vision (WACV), pages 381-389 (2018); and 2) "PPDM: Parallel Point Detection And Matching For Real-Time Human-Object Interaction Detection", Yue Liao, et al., Proceedings of the IEEE/CVF Conference On Computer Vision and Pattern Recognition (CVPR), pages 482-490 (2020).

Although certain specific embodiments are described above for instructional purposes, the teachings of this patent document have general applicability and are not limited to the specific embodiments described above. For example, the same methodology for encouraging a user to continue with an exposure therapy task can be used to motivate a user to continue with physical exercise training, such as weight training with ever more repetitions and/or weight. Accordingly, various modifications, adaptations, and combinations of various features of the described embodiments can be practiced without departing from the scope of the invention as set forth in the claims.

What is claimed is:

1. A method, comprising:
   detecting a situational state of surroundings of a patient while the patient is performing a first task of a cognitive behavioral therapy at a task intensity, wherein the situational state is detected using a sensor of a smartphone used by the patient;
   determining a struggle level experienced by the patient while performing the first task at the task intensity, wherein the struggle level is determined using the sensor of the smartphone used by the patient;
   generating a verbal user prompt, wherein the verbal user prompt has a content and character based on the struggle level and the situational state of the patient while performing the first task at the task intensity, and wherein the verbal user prompt is output by a loudspeaker of the smartphone;
   if the task intensity at which the patient has performed the first task is less than a target intensity level defined for completing the first task, increasing the task intensity at which the patient is prompted to repeat the first task based on the struggle level of the patient while performing the first task if that struggle level does not exceed a maximum allowable struggle level; and
   if the task intensity at which the patient has performed the first task equals or exceeds the target intensity level defined for completing the first task, configuring a second task of the cognitive behavioral therapy based on the struggle level of the patient while performing the first task such that the patient is more likely to complete the second task of the cognitive behavioral therapy.

2. The method of claim 1, wherein the struggle level experienced by the patient while performing the first task is determined based on touch interaction data detected by the sensor on the smartphone during the first task.

3. The method of claim 1, wherein the struggle level is selected from a group consisting of: a level of physical exertion that the patient experiences while performing the first task, and a level of stress that the patient experiences while performing the first task.

4. The method of claim 1, wherein the task intensity is selected from a group consisting of: a length of time during which the patient performs the first task, a proximity to an object that the patient achieves while performing the first task, and a number of repetitions accomplished by the patient while performing the first task.

5. The method of claim 1, wherein the task intensity is a length of time during which the patient touches an object, and wherein the cognitive behavioral therapy involves a controlled exposure of the patient to the object that causes the patient to experience anxiety.

6. The method of claim 1, wherein the second task of the cognitive behavioral therapy is configured based on the struggle level of the patient while performing the first task in a past attempt at completing the first task.

7. The method of claim 1, wherein the verbal user prompt has a content and character generated based on the struggle level of the patient while performing the first task in a past attempt at completing the first task.

8. The method of claim 7, wherein the content and character of the verbal user prompt are generated using machine learning so as to impart a level of reassurance such that the patient is most likely to be motivated to perform the second task of the cognitive behavioral therapy.

9. The method of claim 1, wherein the verbal user prompt is characterized by parameters selected from a group consisting of: a tone of voice, a pitch of voice, a cadence of the verbal user prompt, and a male or female voice.

10. The method of claim 1, wherein the detecting the situational state is performed by a mobile app running on the smartphone.

11. The method of claim 1, wherein the sensor of the smartphone is an accelerometer.

12. A method, comprising:
   selecting a plurality of tasks of a cognitive behavioral therapy, wherein the plurality of tasks includes a first task and a second task;
   prompting a patient to rank the plurality of tasks by task difficulty, wherein the patient ranks the second task to have a greater task difficulty than the first task;
   prompting the patient to perform the first task before prompting the patient to perform the second task;
   detecting a situational state of surroundings of the patient while the patient is performing the first task at a task intensity, wherein the situational state is detected using a sensor of a smartphone used by the patient;
   determining a struggle level experienced by the patient while performing the first task at the task intensity, wherein the struggle level is determined using the sensor of the smartphone used by the patient;
   generating a verbal user prompt, wherein the verbal user prompt has a content and character based on the struggle level and the situational state of the patient while performing the first task at the task intensity;
   if the task intensity at which the patient has performed the first task is less than a target intensity level defined for completing the first task, and if the struggle level of the patient while performing the first task does not exceed a struggle level threshold, increasing the task intensity at which the patient is prompted to repeat the first task based on the struggle level of the patient while performing the first task; and
   if the task intensity at which the patient has performed the first task equals or exceeds the target intensity level defined for completing the first task, configuring the second task based on the struggle level of the patient while performing the first task such that the patient is more likely to complete the second task.

13. The method of claim 12, wherein the struggle level is determined by a mobile app running on the smartphone.

14. The method of claim 12, wherein the detecting the situational state is performed by a mobile app running on the smartphone.

15. The method of claim 12, wherein the verbal user prompt is output by a loudspeaker of the smartphone.

16. The method of claim 12, wherein the verbal user prompt has a content and character generated based on the struggle level of the patient while performing the first task in a past attempt at completing the first task.

17. The method of claim 16, wherein the content and character of the verbal user prompt are generated using machine learning so as to impart a level of reassurance such that the patient is most likely to be motivated to perform the second task.

18. The method of claim 12, wherein the task intensity is selected from a group consisting of: a length of time during which the patient performs the first task, a proximity to an object that the patient achieves while performing the first task, and a number of repetitions accomplished by the patient while performing the first task.

19. The method of claim 12, wherein the task intensity is a length of time during which the patient touches an object, and wherein the cognitive behavioral therapy involves a controlled exposure of the patient to the object that causes the patient to experience anxiety.

20. The method of claim 12, wherein the second task of the cognitive behavioral therapy is configured based on the struggle level of the patient while performing the first task in a past attempt at completing the first task.

* * * * *